(12) United States Patent
Azad et al.

(10) Patent No.: US 10,526,350 B2
(45) Date of Patent: Jan. 7, 2020

(54) PROCESS FOR THE PREPARATION OF BARICITINIB AND AN INTERMEDIATE THEREOF

(71) Applicant: SUN PHARMACEUTICAL INDUSTRIES LIMITED, Mumbai, Maharashtra (IN)

(72) Inventors: Md Abul Kalam Azad, Karimgang (IN); Gyanendra Pandey, Faridabad (IN); Kaptan Singh, Gurgaon (IN); Mohan Prasad, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 135 days.

(21) Appl. No.: 15/548,116

(22) PCT Filed: Feb. 2, 2016

(86) PCT No.: PCT/IB2016/050529
§ 371 (c)(1),
(2) Date: Aug. 2, 2017

(87) PCT Pub. No.: WO2016/125080
PCT Pub. Date: Aug. 11, 2016

(65) Prior Publication Data
US 2019/0100538 A1    Apr. 4, 2019

(30) Foreign Application Priority Data
Feb. 2, 2015 (IN) .............................. 289/DEL/2015

(51) Int. Cl.
C07F 5/04    (2006.01)
C07D 487/04  (2006.01)
C07D 403/06  (2006.01)
C07D 205/06  (2006.01)

(52) U.S. Cl.
CPC .............. *C07F 5/04* (2013.01); *C07D 205/06* (2013.01); *C07D 403/06* (2013.01); *C07D 487/04* (2013.01)

(58) Field of Classification Search
CPC .................... C07F 5/02; A61K 31/69
See application file for complete search history.

(56) References Cited

U.S. PATENT DOCUMENTS 8,158,616 B2    4/2012    Rodgers et al.

FOREIGN PATENT DOCUMENTS

| WO | WO 2014/028756 A1 | 8/2013 |
| WO | WO 2015/145286 A1 | 3/2015 |
| WO | WO 2016/125080 A3 | 2/2016 |

OTHER PUBLICATIONS

International Search Report and Written Opinion for International Application No. PCT/IB2016/050529, issued by WIPO dated Jul. 22, 2016.
International Preliminary Report on Patentability for International Application No. PCT/IB2016/050529, issued by WIPO dated Aug. 8, 2017.
European Extended Search Report for European Application No. 16746200.1, issued by EPO dated May 23, 2018.

*Primary Examiner* — Susanna Moore
(74) *Attorney, Agent, or Firm* — Stanley Liang, Esq.; Liang & Hennessey LLP

(57) ABSTRACT

The present invention provides processes for the preparation of baricitinib of Formula I and an intermediate of Formula V. The present invention also provides the use of the intermediate of Formula V for the preparation of baricitinib.

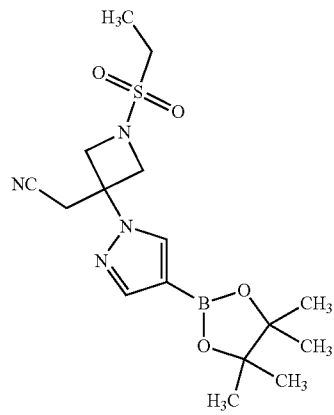

Formula V

13 Claims, No Drawings

PROCESS FOR THE PREPARATION OF BARICITINIB AND AN INTERMEDIATE THEREOF

FIELD OF THE INVENTION

The present invention provides processes for the preparation of baricitinib of Formula I and an intermediate of Formula V. The present invention also provides the use of the intermediate of Formula V for the preparation of baricitinib.

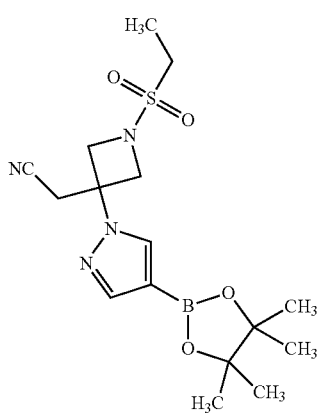

Formula V

BACKGROUND OF THE INVENTION

Baricitinib is a Janus kinase (JAK) inhibitor. It is chemically designated as {1-(ethylsulfonyl)-3-[4-(7H-pyrrolo[2,3-d]pyrimidin-4-yl)-1H-pyrazol-1-yl]azetidin-3-yl}acetonitrile, having the structure as depicted in Formula I.

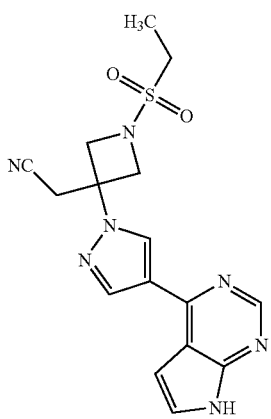

Formula I

U.S. Pat. No. 8,158,616 discloses a process for the preparation of baricitinib comprising the reaction of 2-(1-(ethylsulfonyl)azetidin-3-ylidene)acetonitrile of Formula II with 4-(1H-pyrazol-4-yl)-7H-pyrrolo[2,3-d]pyrimidin-7-yl methyl pivalate of Formula III to provide an intermediate of Formula IV, followed by deprotection of the intermediate of Formula IV to obtain baricitinib of Formula I, as depicted in Scheme I below:

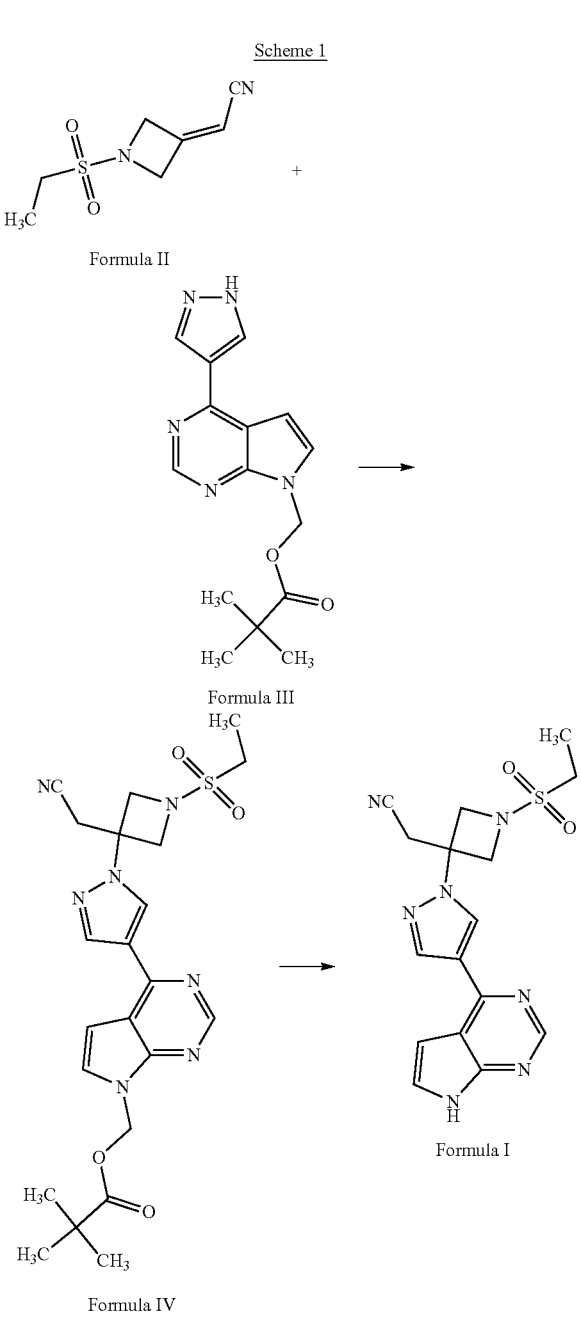

The process disclosed in U.S. Pat. No. 8,158,616 requires a deprotection step in the last stage of the synthesis, which adds to the cost of the overall synthesis.

Thus, there exists a need for an alternate, cost-effective, and industrially advantageous process for the preparation of baricitinib.

SUMMARY OF THE INVENTION

The present invention provides an environmentally friendly, cost-effective, and industrially advantageous process for the preparation of baricitinib of Formula I. The process of the present invention involves the use of an environmentally benign heterogeneous catalyst, such as a zeolite. The use of a zeolite as a catalyst is beneficial for large scale synthesis, owing to its inexpensive nature, ease of handling, ease of isolation of the product, high reaction yields, and recyclability. Further, the process of the present invention involves the use of {1-(ethylsulfonyl)-3-[4-(4,4,5,5-tetramethyl-1,3,2-dioxaborolan-2-yl)-H-pyrazol-1-yl]azetidin-3-yl}acetonitrile of Formula V as an intermediate for the preparation of baricitinib of Formula I, which makes the entire process unique.

Formula V

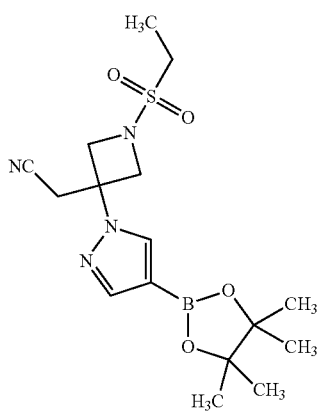

A first aspect of the present invention provides a process for the preparation of baricitinib of Formula I, Formula I

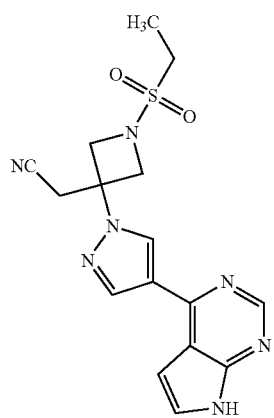

comprising the steps of:

i) reacting tert-butyl 3-(cyanomethylidene)azetidine-1-carboxylate of Formula VI Formula VI

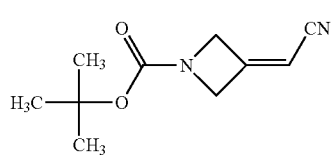

with a zeolite to obtain 3-(cyanomethylene)azetidine hydrochloride of Formula VII;

Formula VII

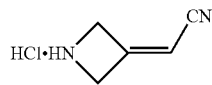

ii) reacting the 3-(cyanomethylene)azetidine hydrochloride of Formula VII with ethanesulfonyl chloride to obtain 2-(1-(ethylsulfonyl)azetidin-3-ylidene)acetonitrile of Formula II;

Formula II

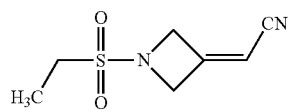

iii) reacting the 2-(1-(ethylsulfonyl)azetidin-3-ylidene)acetonitrile of Formula II with 4-(4,4,5,5-tetramethyl-1,3,2-dioxaborolan-2-yl)-1H-pyrazole of Formula VIII Formula VIII

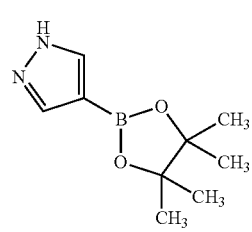

to obtain {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V; and Formula V

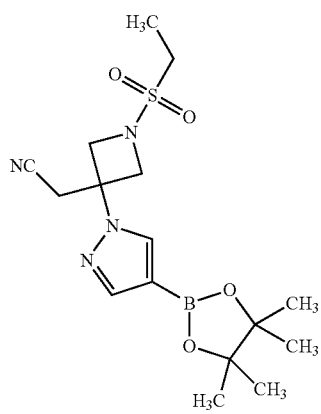

iv) reacting the {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V with 4-chloro-7H-pyrrolo[2,3-d]pyrimidine of Formula IX

Formula IX to obtain baricitinib of Formula I.

A second aspect of the present invention provides a process for the preparation of {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V,

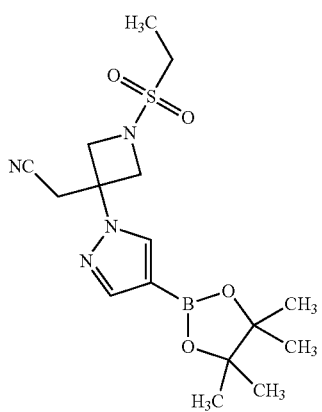

Formula V comprising the steps of:

i) reacting tert-butyl 3-(cyanomethylidene)azetidine-1-carboxylate of Formula VI

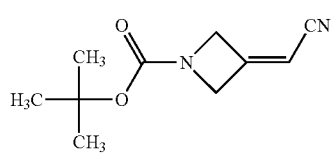

Formula VI with a zeolite to obtain 3-(cyanomethylene)azetidine hydrochloride of Formula VII;

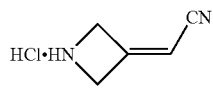

Formula VII ii) reacting the 3-(cyanomethylene)azetidine hydrochloride of Formula VII with ethanesulfonyl chloride to obtain 2-(1-(ethylsulfonyl)azetidin-3-ylidene)acetonitrile of Formula II; and

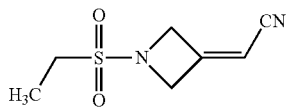

Formula II iii) reacting the 2-(1-(ethylsulfonyl)azetidin-3-ylidene)acetonitrile of Formula II with 4-(4,4,5,5-tetramethyl-1,3,2-dioxaborolan-2-yl)-1H-pyrazole of Formula VIII

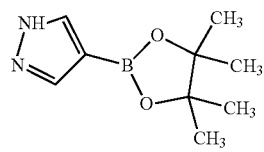

Formula VIII to obtain {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V.

A third aspect of the present invention provides a process for the preparation of baricitinib of Formula I,

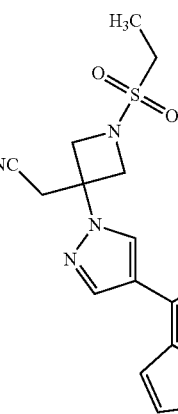

Formula I comprising reacting {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V

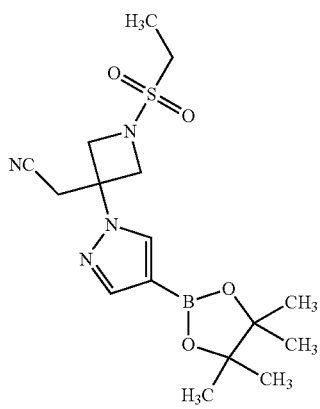

Formula V with 4-chloro-7H-pyrrolo[2,3-d]pyrimidine of Formula IX

Formula IX to obtain baricitinib of Formula I.

A fourth aspect of the present invention provides a compound of Formula V.

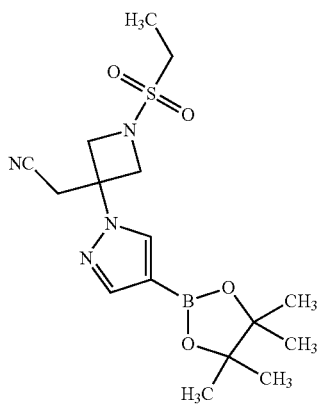

Formula V

A fifth aspect of the present invention provides a compound of Formula V

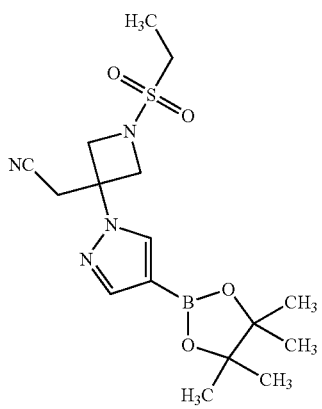

Formula V for the use as an intermediate for the preparation of baricitinib.

DETAILED DESCRIPTION OF THE INVENTION

Various embodiments and variants of the present invention are described hereinafter.

The term "about", as used herein, refers to any value which lies within the range defined by a number up to ±10% of the value.

The term "ambient temperatures," as used herein, refers to a temperature in the range of about 20° C. to about 35° C.

The term "zeolite," as used herein, refers to natural or modified aluminosilicates, such as montmorillonite K-10 and montmorillonite KSF.

Examples of solvents to be used for the processes of the present invention include solvents selected from the group consisting of alcohols, hydrocarbons, ethers, chlorinated hydrocarbons, ketones, amides, sulphoxides, water, nitriles, and mixtures thereof. Examples of alcohols include methanol, ethanol, n-propanol, and iso-propanol. Examples of hydrocarbons include benzene, toluene, and xylene. Examples of ethers include diethyl ether, ethyl methyl ether, di-isopropyl ether, tetrahydrofuran, and 1,4-dioxane. Examples of chlorinated hydrocarbons include dichloromethane and chloroform. Examples of ketones include acetone, dimethyl ketone, ethyl methyl ketone, and methyl iso-butyl ketone. Examples of amides include N,N-dimethylformamide and N,N-dimethylacetamide. Examples of sulphoxides include dimethyl sulphoxide and diethyl sulphoxide. Examples of nitriles include acetonitrile, propionitrile, and benzonitrile.

Examples of bases to be used for the processes of the present invention include inorganic and organic bases. Examples of inorganic bases include alkali and alkaline earth metal hydroxides, carbonates, and bicarbonates. Examples of alkali and alkaline earth metal hydroxides include lithium hydroxide, sodium hydroxide, potassium hydroxide, magnesium hydroxide, calcium hydroxide, and barium hydroxide. Examples of alkali and alkaline earth metal carbonates include sodium carbonate, potassium carbonate, calcium carbonate, and magnesium carbonate. Examples of alkali and alkaline earth metal bicarbonates include sodium bicarbonate and potassium bicarbonate. Examples of organic bases include N,N-diisopropylethylamine, triethylamine, triisopropylamine, N,N-2-trimethyl-2-propanamine, N-methylmorpholine, 4-dimethylaminopyridine, 2,6-di-tert-butyl-4-dimethylaminopyridine, 1,4-diazabicyclo[2.2.2]octane, and 1,8-diazabicyclo[5.4.0]undec-7-ene.

The tert-butyl 3-(cyanomethylene)azetidine-1-carboxylate of Formula VI and the 4-(4,4,5,5-tetramethyl-1,3,2-dioxaborolan-2-yl)-1H-pyrazole of Formula VIII can be prepared by the process disclosed in U.S. Pat. No. 8,158,616.

The 4-chloro-7H-pyrrolo[2,3-d]pyrimidine of Formula IX is available commercially.

The reaction of the tert-butyl 3-(cyanomethylidene)azetidine-1-carboxylate of Formula VI with a zeolite and hydrochloric acid to obtain 3-(cyanomethylene)azetidine hydrochloride of Formula VII is carried out in a solvent. The solvent is selected from the solvents described hereinbefore. The reaction is carried out between ambient temperature and reflux temperature of the solvent for about 5 hours to about 24 hours. In an embodiment of the present invention, the zeolite used is montmorillonite K-10 and the solvent used is methanol.

The reaction of the 3-(cyanomethylene)azetidine hydrochloride of Formula VII with ethanesulfonyl chloride to obtain the 2-(1-(ethylsulfonyl)azetidin-3-ylidene)acetonitrile of Formula II can be carried as per the process described in U.S. Pat. No. 8,158,616

The reaction of the 2-(1-(ethylsulfonyl)azetidin-3-ylidene)acetonitrile of Formula II with the 4-(4,4,5,5-tetramethyl-1,3,2-dioxaborolan-2-yl)-1H-pyrazole of Formula VIII to obtain the {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V can be carried out in the presence of a base in a solvent. The solvent and base are selected from the solvents and bases described hereinbefore. The reaction is carried out between ambient temperature and the reflux temperature of the solvent for about 5 hours to about 24 hours. In an embodiment of the present invention, the base used is potassium carbonate and the reaction is carried out at ambient temperature for about 16 hours to about 18 hours.

The reaction of the {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V with the 4-chloro-7H-pyrrolo[2,3-d]pyrimidine of Formula IX to obtain baricitinib of Formula I can be carried out in the presence of a base in a solvent. The solvent and base are selected from the solvents and bases described hereinbefore. In an embodiment of the present invention, the base used is potassium carbonate. The reaction of the {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V with the 4-chloro-7H-pyrrolo[2,3-d]pyrimidine of Formula IX is initiated by adding a palladium catalyst. Examples of palladium catalysts include tetrakis(triphenylphosphine)palladium(0) and tetrakis(tri(o-tolyl)phosphine)palladium(0). In an embodiment of the present invention, tetrakis(triphenylphosphine)palladium(0) is used. The reaction is carried out between ambient temperature and the reflux temperature of the solvent for about 5 hours to about 24 hours. In an embodiment of the present invention, the reaction is carried out at the reflux temperature of the solvent for about 4 hours to about 6 hours.

While the present invention has been described in terms of its specific aspects and embodiments, certain modifications and equivalents will be apparent to those skilled in the art, and are intended to be included within the scope of the present invention.

The following examples are for illustrative purposes only and should not be construed as limiting the scope of the invention in any way

EXAMPLES

Example 1: Preparation of 3-(cyanomethylene)azetidine hydrochloride (Formula VII)

Aqueous hydrochloric acid (6N, 10 mL) and montmorillonite K-10 (2 g) were added into a reaction vessel at ambient temperature. The contents were stirred for 1 hour, and then filtered under reduced pressure to obtain activated montmorillonite K-10. The activated montmorillonite K-10 was added into another reaction vessel containing tert-butyl 3-(cyanomethylidene)azetidine-1-carboxylate (2 g; Formula VI) and methanol (20 mL) at ambient temperature. The reaction mixture was refluxed for about 12 hours to about 15 hours. On completion, the reaction mixture was filtered under reduced pressure followed by recovery of methanol under reduced pressure at about 40° C. to about 45° C. to obtain 3-(cyanomethylene)azetidine hydrochloride.

Yield: 75%

Example 2: Preparation of 2-(1-(ethylsulfonyl)azetidin-3-ylidene)acetonitrile (Formula II)

N,N-Di isopropylethylamine (4.5 mL) was added into a reaction vessel containing acetonitrile (50 mL) and 3-(cyanomethylene)azetidine hydrochloride (1.5 g; Formula VII) at about 0° C. to about 10° C. The reaction mixture was stirred for about 10 minutes. Ethanesulfonyl chloride (2.22 g) was added into the reaction mixture at about 0° C. to about 5° C. over about 5 minutes. The temperature of the reaction mixture was raised to about 20° C. to about 25° C., and then the reaction mixture was stirred for about 16 hours. On completion of the reaction, acetonitrile was recovered from the reaction mixture under reduced pressure at about 40° C. to about 45° C. to obtain an oily residue. Dichloromethane (50 mL) was added into the residue. The contents were washed with a saturated sodium chloride solution (30 mL), followed by complete recovery of dichloromethane under reduced pressure at about 40° C. to obtain 2-(1-(ethylsulfonyl)azetidin-3-ylidene)acetonitrile.

Yield: 98.59%

Example 3: Preparation of {1-(ethylsulfonyl)-3-[4-(4,4,5,5-tetramethyl-1,3,2-dioxaborolan-2-yl)-1H-pyrazol-1-yl]azetidin-3-yl}acetonitrile (Formula V)

1,4-Dioxane (20 mL) was added into a reaction vessel containing a solution of potassium carbonate (4.5 g) in water (30 mL) at about 20° C. to about 25° C. 2-(1-(Ethylsulfonyl) azetidin-3-ylidene)acetonitrile (2 g; Formula II) and 4-(4,4,5,5-tetramethyl-1,3,2-dioxaborolan-2-yl)-1H-pyrazole (2.30 g; Formula VIII) were added into the reaction mixture at about 20° C. to about 25° C. The reaction mixture was stirred at about 20° C. to about 25° C. for about 16 hours to about 18 hours. On completion of the reaction, 1,4-dioxane was recovered from the reaction mixture under reduced pressure at about 45° C. to obtain a residue. Ethyl acetate (20 mL) was added into the residue, and the contents were stirred for about 5 minutes. The organic and aqueous layers were separated. The organic layer was concentrated under reduced pressure at about 45° C. to obtain {1-(ethylsulfonyl)-3-[4-(4,4,5,5-tetramethyl-1,3,2-dioxaborolan-2-yl)-1H-pyrazol-1-yl]azetidin-3-yl}acetonitrile.

Yield: 85.78%

Mass: 381.4 $[M+H]^+$

Example 4: Preparation of Baricitinib (Formula I)

4-Chloro-7H-pyrrolo[2,3-d]pyrimidine (0.8 g; Formula IX) was added into a reaction vessel containing a solution of potassium carbonate (2.1 g) in water (30 mL) at about 20° C. to about 25° C. A solution of {1-(ethylsulfonyl)-3-[4-(4,4,5,5-tetramethyl-1,3,2-dioxaborolan-2-yl)-1H-pyrazol-1-yl]azetidin-3-yl}acetonitrile (2.0 g; Formula V) in 1,4-dioxane (30 mL) was added into the reaction mixture at about 20° C. to about 25° C., followed by the addition of tetrakis (triphenylphosphine)palladium(0) (0.1 g). The reaction mixture was stirred at about 80° C. to about 85° C. for about 5 hours. On completion of the reaction, 1,4-dioxane was recovered from the reaction mixture under reduced pressure at about 45° C. to obtain a residue. Ethyl acetate (50 mL) was added into the residue, and then the contents were stirred for about 5 minutes. The organic and aqueous layers we separated. The organic layer was concentrated under reduced pressure at about 45° C. to obtain baricitinib.

Yield: 99.0%

We claim:

1. A process for the preparation of {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V, Formula V

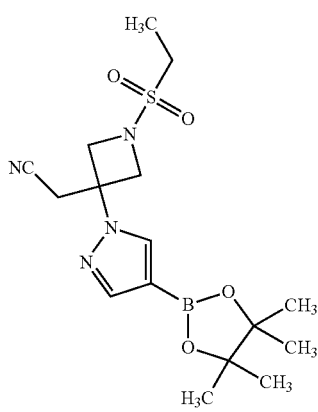

comprising the steps of:
i) reacting tert-butyl 3-(cyanomethylidene)azetidine-1-carboxylate of Formula VI Formula VI

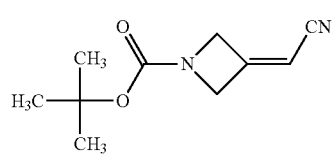

with a zeolite to obtain 3-(cyanomethylene)azetidine hydrochloride of Formula VII;

Formula VII

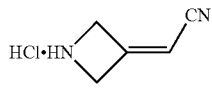

ii) reacting the 3-(cyanomethylene)azetidine hydrochloride of Formula VII with ethanesulfonyl chloride to obtain 2-(1-(ethylsulfonyl)azetidin-3-ylidene)acetonitrile of Formula II; and Formula II

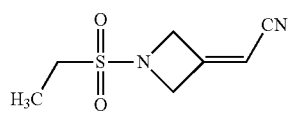

iii) reacting the 2-(1-(ethylsulfonyl)azetidin-3-ylidene)acetonitrile of Formula II with 4-(4,4,5,5-tetramethyl-1,3,2-dioxaborolan-2-yl)-1H-pyrazole of Formula VIII Formula VIII

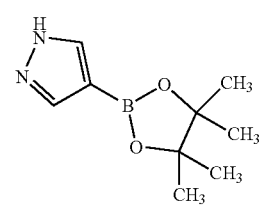

to obtain {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V.

2. A process for the preparation of baricitinib of Formula I,

Formula I

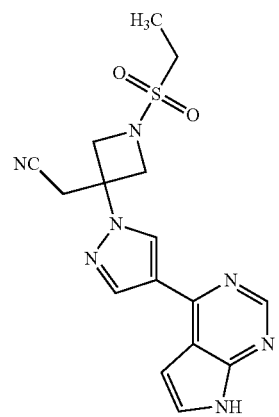

comprising the steps of:
i) reacting tert-butyl 3-(cyanomethylidene)azetidine-1-carboxylate of Formula VI Formula VI

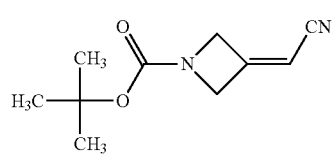

with a zeolite to obtain 3-(cyanomethylene)azetidine hydrochloride of Formula VII;

Formula VII

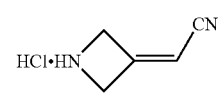

ii) reacting the 3-(cyanomethylene)azetidine hydrochloride of Formula VII with ethanesulfonyl chloride to obtain 2-(1-(ethylsulfonyl)azetidin-3-ylidene)acetonitrile of Formula II;

Formula II

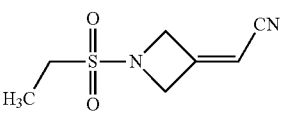

iii) reacting the 2-(1-(ethylsulfonyl)azetidin-3-ylidene)acetonitrile of Formula II with 4-(4,4,5,5-tetramethyl-1,3,2-dioxaborolan-2-yl)-1H-pyrazole of Formula VIII

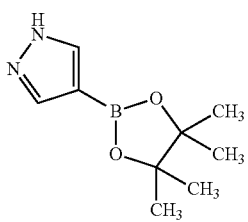

Formula VIII to obtain {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V; and

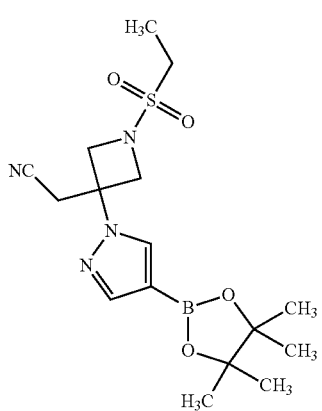

Formula V iv) reacting the {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V with 4-chloro-7H-pyrrolo[2,3-d]pyrimidine of Formula IX

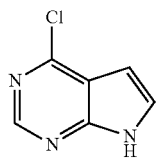

Formula IX to obtain baricitinib of Formula I.

3. The process according to claim 1, wherein the reaction of the tert-butyl 3-(cyanomethylidene)azetidine-1-carboxylate of Formula VI with a zeolite is carried out in a solvent selected from the group consisting of alcohols, hydrocarbons, ethers, chlorinated hydrocarbons, ketones, amides, sulphoxides, water, nitriles, and mixtures thereof.

4. The process according to claim 3, wherein the reaction is carried out in methanol.

5. The process according to claim 1, wherein the reaction of the 2-(1-(ethylsulfonyl)azetidin-3-ylidene)acetonitrile of Formula II with the 4-(4,4,5,5-tetramethyl-1,3,2-dioxaborolan-2-yl)-1H-pyrazole of Formula VIII is carried out in the presence of an inorganic or organic base in a solvent.

6. The process according to claim 5, wherein the base is potassium carbonate.

7. The process according to claim 5, wherein the solvent is selected from the group consisting of alcohols, hydrocarbons, ethers, chlorinated hydrocarbons, ketones, amides, sulphoxides, water, nitriles, and mixtures thereof.

8. The process according to claim 1, wherein the reaction of the 2-(1-(ethylsulfonyl)azetidin-3-ylidene)acetonitrile of Formula II with the 4-(4,4,5,5-tetramethyl-1,3,2-dioxaborolan-2-yl)-1H-pyrazole of Formula VIII is carried out at ambient temperature to the reflux temperature of the solvent.

9. The process according to claim 2, wherein the reaction of the {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V with the 4-chloro-7H-pyrrolo[2,3-d]pyrimidine of Formula IX is carried out in the presence of an inorganic or organic base in a solvent.

10. The process according to claim 9, wherein the base is potassium carbonate.

11. The process according to claim 9, wherein the solvent is selected from the group consisting of alcohols, hydrocarbons, ethers, chlorinated hydrocarbons, ketones, amides, sulphoxides, water, nitriles, and mixtures thereof.

12. The process according to claim 2, wherein the reaction of the {1-(ethylsulfonyl)-3-[4-(4,4,5,5-tetramethyl-1,3,2-dioxaborolan-2-yl)-1H-pyrazol-1-yl]azetidin-3-yl}acetonitrile of Formula V with the 4-chloro-7H-pyrrolo[2,3-d]pyrimidine of Formula IX is carried out between ambient temperature and reflux temperature of the solvent.

13. A compound of Formula V,

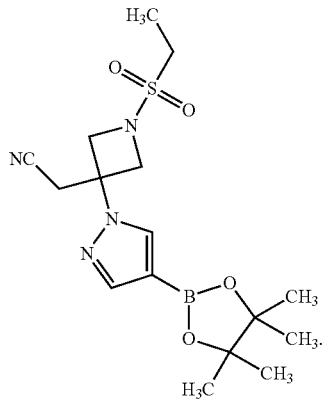

Formula V

* * * * *